United States Patent
Uhrich

(10) Patent No.: US 7,396,527 B2
(45) Date of Patent: Jul. 8, 2008

(54) ANTIBIOTIC POLYMERS

(75) Inventor: Kathryn E. Uhrich, Plainfield, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 430 days.

(21) Appl. No.: 10/913,289

(22) Filed: Aug. 6, 2004

(65) Prior Publication Data

US 2005/0100526 A1 May 12, 2005

Related U.S. Application Data

(63) Continuation of application No. PCT/US03/03818, filed on Feb. 7, 2003.

(60) Provisional application No. 60/355,025, filed on Feb. 7, 2002.

(51) Int. Cl.
*A61K 31/74* (2006.01)

(52) U.S. Cl. .................................. 424/78.17; 424/78.19

(58) Field of Classification Search .............. 424/78.17, 424/78.19
See application file for complete search history.

(56) References Cited

U.S. PATENT DOCUMENTS 6,051,255 A 4/2000 Conley et al. ................ 424/482

FOREIGN PATENT DOCUMENTS

WO WO-00/59515 10/2000

OTHER PUBLICATIONS

Merck Index, 12th ed., 1996, pp. 619 and 2404-.*

Yagmurlu, et al., "Sulbactam-Cefoperazone Polyhydroxybutyrate-co-Hydroxyvalerate(PHBV) Local Antibiotic Delivery System:In Vivo Effectiveness and Biocompatibity in the Treatment of Implant-Related Experimental Osteomyelitis", *Journal of Biomedical Materials Research*,46, Abstract Only, Obtained from Medline, Accession No. 1999326670,(Sep. 15, 1999),494-503.

Leong et al., "Synthesis of Polyanhydrides: Melt-Polycondensation, Dehydrochlorination, and Dehydrative Coupling", *Macromolecules*, 20(4), 705-712, (Apr. 1987).

Yu et al., "Poly(N-Acetyl Dopamine Sebacate): A New Polymeric Prodrug of Dopamine", *Proceed. Intern. Symp. Control. Rel. Bioact. Mater.*, 21, 351-352 (1994).

* cited by examiner

*Primary Examiner*—Michael G. Hartley
*Assistant Examiner*—James Rogers
(74) *Attorney, Agent, or Firm*—Viksnins Harris & Padys PLLP

(57) ABSTRACT

Polymers (i.e. polyesters, polyamides, polythioesters, polyanhydrides, or a mixture thereof) which degrade hydrolytically to provide a combination of a beta-lactam antibiotic (e.g., amoxicillin) and a beta-lactamase inhibitor (e.g., clavulanic acid) (or a pharmaceutically acceptable salt thereof) are provided. Methods of producing these polymers, intermediates useful for preparing these polymers, and methods of using these polymers to deliver a combination of a beta-lactam antibiotic and a beta-lactamase inhibitor (or a pharmaceutically acceptable salt thereof) to a host are also provided.

22 Claims, No Drawings

ANTIBIOTIC POLYMERS

This application is a continuation under 35 U.S.C. 111(a) of International Application No. PCT/US03/03818, filed Feb. 7, 2003 and published in English as WO 03/066053 on Aug. 14, 2003, which claimed priority from Provisional Application No. 60/355,025, filed Feb. 7, 2002.

BACKGROUND OF THE INVENTION

The first antibiotic was penicillin, which is now classified in the structural family of beta-lactam antibiotics. The beta-lactam antibiotics contain a beta-lactam ring, and generally act by inhibiting bacterial cell wall synthesis. Since the discovery of penicillin, hundreds of beta-lactam antibiotics have been isolated from natural sources or chemically synthesized. Beta-lactam antibiotics are still used widely to combat infections.

However, bacteria increasingly develop resistance to beta-lactam antibiotics. Resistance most often arises from beta-lactamase enzymes that degrade the antibiotics. To overcome the resistance, physicians sometimes administer compounds that inhibit beta-lactamase enzymes, known as beta-lactamase inhibitors, in conjunction with beta-lactam antibiotics. One commercially available combination of a beta-lactam antibiotic and a beta-lactamase inhibitor is Augmentin® (amoxicillin/clavulanate potassium), which contains the beta-lactam antibiotic amoxicillin and the beta-lactamase inhibitor clavulanic acid.

Augmentin® (amoxicillin/clavulanate potassium), and other beta-lactam antibiotic/beta-lactamase inhibitor combinations are typically administered orally or by systemic intravenous injection. Both these methods of administration require repeated administrations over a course of several days. This carries a risk of missed doses and patient non-compliance with finishing the course of therapy. Local administration is also sometimes desired to treat a localized infection. New formulations or methods for administering a combination of a beta-lactam antibiotic and a beta-lactamase inhibitor are currently needed. Preferably the new formulations would allow less frequent administration, would reduce the likelihood of patient non-compliance with finishing a course of therapy, or would allow sustained release. Preferably such new formulation might also allow local administration to a site of infection or a site at risk for infection, thereby reducing systemic exposure to the beta-lactam antibiotic, the beta-lactamase inhibitor, or both.

SUMMARY OF THE INVENTION

The present invention provides polymers that degrade in the body to release a beta-lactam antibiotic and a beta-lactamase inhibitor. The polymers can provide sustained release of the beta-lactam antibiotic and/or the beta-lactamase inhibitor, thereby reducing the frequency that the polymers need to be administered compared to other beta-lactam antibiotic/beta-lactamase inhibitor combination formulations. In certain embodiments, the polymers can comprise an entire course of therapy, thereby reducing or eliminating the risk of a patient not completing a course of therapy. The polymers can also facilitate local administration of a beta-lactam antibiotic/beta-lactamase inhibitor combination. For instance, articles to be inserted in the body that are potential sites for bacterial growth can be coated with or be composed of the polymers to provide for local administration of the beta-lactam antibiotic/beta-lactamase inhibitor combination at a site of potential infection.

Polyesters, polythioesters, polyamides, and polyanhydrides which degrade into a combination of a beta-lactam antibiotic (e.g. amoxicillin) and a beta-lactamase inhibitor (e.g. clavulanic acid), or salts thereof have now been developed. Accordingly, the invention provides a polymer of the invention comprising a backbone, wherein the polymer comprises (i) a group that will yield a beta-lactam antibiotic or a pharmaceutically acceptable salt thereof, and (ii) a group that will yield a beta-lactamase inhibitor or a pharmaceutically acceptable salt thereof, upon hydrolysis of the polymer; wherein the group that will yield a beta-lactam antibiotic or a pharmaceutically acceptable salt thereof, or the group that will yield the beta-lactamase inhibitor or a pharmaceutically acceptable salt thereof is chemically incorporated into the backbone of the polymer.

Preferably, the group that will yield a beta-lactam antibiotic and the group that will yield a beta-lactam antibiotic, if they are chemically incorporated into the backbone or chemically appended to the polymer are incorporated or appended by bonds that are hydrolyzable, either enzymatically or non-enzymatically following administration to a host.

The invention also provides a polymer of the invention that is a polymer comprising a backbone, wherein the backbone comprises one or more groups that will each independently yield a beta-lactam antibiotic and a beta-lactamase inhibitor, a pharmaceutically acceptable salt thereof, or a combination thereof, upon hydrolysis of the polymer.

In the polymers of the invention, the beta-lactam antibiotic and the beta-lactamase inhibitor are not the same compound (i.e., a beta-lactam antibiotic that also inhibits beta-lactamase).

The invention also provides a pharmaceutical composition comprising a polymer of the invention and a pharmaceutically acceptable carrier.

The invention also provides a method for killing or inhibiting bacteria comprising contacting the bacteria with an effective amount of a polymer of the present invention.

The invention also provides a method for treating a bacterial infection in a mammal comprising administering to a mammal in need of such treatment an effective amount of a polymer of the present invention.

The invention also provides a method of delivering a combination of a beta-lactam antibiotic (e.g. amoxicillin) and a beta-lactamase inhibitor (e.g. clavulanic acid), or a pharmaceutically acceptable salt thereof, to a host comprising administering to the host a biocompatible and biodegradable polymer of the invention, which degrades thereby providing a combination of a beta-lactam antibiotic and a beta-lactamase inhibitor, or a pharmaceutically acceptable salt thereof.

The invention provides a polymer of the invention for use in medical therapy, as well as the use of a polymer of the invention for the manufacture of a medicament useful for treating a bacterial infection in a mammal, such as a human.

The invention also provides processes and intermediates disclosed herein that are useful for preparing a polymer of the invention.

DETAILED DESCRIPTION OF THE INVENTION

Definitions

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_6$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "beta-lactam antibiotic" refers to a compound having anti-bacterial activity that contains the beta-lactam or 2-azetidine ring structure shown below.

Beta-lactam antibiotics typically act by inhibiting bacterial cell wall synthesis.

The term "beta-lactamase inhibitor" refers to a compound that inhibits the activity of a beta-lactamase, which is an enzyme that degrades and thereby inactivates a beta-lactam antibiotic. Beta-lactamase inhibitors typically contain the beta-lactam ring structure but have greater activity as inhibitors of beta-lactamase than as antibiotics.

Any beta-lactam antibiotic and beta-lactamase inhibitor with suitable functionality (as discussed hereinbelow) can be incorporated into a polymer of the invention.

The term "treatment" as used herein includes any treatment of an infection in an animal, particularly a mammal, more particularly a human, and includes:

(i) preventing the infection from occurring in a subject which may be at risk for the infection but has not yet been diagnosed as having it;

(ii) inhibiting the infection or a condition associated with it, i.e. slowing or arresting the development of the infection; relieving the symptoms associated with the infection, or causing regression of the infection.

The term ester linkage means —OC(=O)— or —C(=O)O—; the term ester linkage includes an aryl ester linkage; the term thioester linkage means —SC(=O)— or —C(=O)S—; and the term amide linkage means —N(R)C(=O)— or —C(=O)N(R)—, wherein each R is a suitable organic radical, such as, for example, hydrogen, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$)alkyl, or heteroaryl($C_1$-$C_6$)alkyl; the term phosphate ester linkage means —P(=O)(OH)O— or —OP(=O)(OH)—, the term sulfate ester linkage means —S(=O)(=O)O—, or —OS(=O)(OH)—.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an α-methylbenzyl amide). Other suitable amino and carboxy protecting groups are known to those skilled in the art (See for example, Greene, T. W.; Wutz, P. G. M. "Protecting Groups In Organic Synthesis" second edition, 1991, New York, John Wiley & sons, Inc., and references cited therein).

The term "host" includes animals (e.g., mammals such as humans) and plants.

The term "peptide" describes a sequence of 2 to about 35 amino acids (e.g. as defined herein above) or peptidyl residues. The sequence may be linear or cyclic. For example, a cyclic peptide can be prepared or may result from the formation of disulfide bridges between two cysteine residues in a sequence. Preferably a peptide comprises about 3 to about 20, or about 5 to about 15 amino acids. Peptide derivatives can be prepared as disclosed in U.S. Pat. Nos. 4,612,302; 4,853,371; and 4,684,620, or as described in the Examples herein below. Peptide sequences specifically recited herein are written with the amino terminus on the left and the carboxy terminus on the right.

The term "chemically incorporated" into the backbone of a polymer refers to a group that is held in the backbone of a polymer by two covalent bonds. The bonds may be formed in any manner, e.g., synthetically or biologically. The term "chemically appended" to a polymer refers to a group that does not form part of the backbone of the polymer and that is attached to the polymer by at least one covalent bond. The bond my be formed in any manner.

Polymers of the Invention

The biocompatible, biodegradable polyesters, polythioesters, polyamides, and polyanhydrides of the invention are useful in a variety of applications where delivery of a combination of a beta-lactam antibiotic and a beta-lactamase inhibitor is desired. Examples of such applications include, but are not limited to, medical, dental and cosmetic uses.

The polymers of the invention may be prepared in accordance with methods commonly employed in the field of synthetic polymers to produce a variety of useful products with valuable physical and chemical properties. The polymers can be readily processed into pastes or solvent cast to yield films, coatings, microspheres and fibers with different geometric shapes for design of various medical implants, and may also be processed by compression molding and extrusion.

Guidance in techniques for preparing polymers of the invention can be found in WO 02/009767, WO 02/009768, WO 99/12990, and in U.S. patent application Ser. No. 09/627, 215, now U.S. Pat. No. 6,486,214.

Medical implant applications include the use of polyesters, polythioesters, polyamides, or polyanhydrides to coat or to form shaped articles such as vascular grafts and stents, bone plates, sutures, implantable sensors, implantable drug delivery devices, stents for tissue regeneration, and other articles that decompose into non-toxic components within a known time period.

Polymers of the present invention can also be incorporated into oral formulations and into products such as skin moisturizers, cleansers, pads, plasters, lotions, creams, gels, ointments, solutions, shampoos, tanning products and lipsticks for topical application.

Although the invention provides homopolymers and/or copolymers that are prepared from suitably functionalized beta-lactam antibiotics (e.g. amoxicillin), beta-lactamase inhibitors (e.g. clavulanic acid), or a combination thereof, it has been discovered that the mechanical and hydrolytic properties of polymers can be controlled by also incorporating a linking group (L) into the polymer backbone.

Preferably, the polymers of the invention comprise backbones wherein the beta-lactam antibiotic, the beta-lactamase inhibitor, or a combination thereof and linker groups are bonded together through ester linkages, thioester linkages, amide linkages, anhydride linkages or a mixture thereof. Due to the presence of the ester, thioester, anhydride and/or amide linkages, the polymers can be hydrolyzed under physiological conditions to provide a beta-lactam antibiotic (e.g. amoxicillin) or a pharmaceutically acceptable salt thereof, a beta-lactamase inhibitor (e.g. clavulanic acid) or a pharmaceutically acceptable salt thereof, or a combination thereof. Thus, the polymers of the invention can be particularly useful as a controlled release source for a beta-lactam antibiotic, a beta-lactamase inhibitor, a pharmaceutically acceptable salt thereof, or a combination thereof, or as a medium for the localized delivery of a beta-lactam antibiotic, a beta-lactamase inhibitor, pharmaceutically acceptable salts thereof, or a combination thereof to a selected site. For example, the polymers of the invention can be used for the localized delivery to a selected site within the body of a human patient (e.g., within or near the lower respiratory system), where the degradation of the polymer provides localized, controlled, release.

Amoxicillin/Clavulanic Acid

In a preferred embodiment, the beta-lactam antibiotic is amoxicillin and the beta-lactamase inhibitor is clavulanic acid. As used herein, "amoxicillin" refers to the semisynthetic antibiotic chemically designated as (2S,5R,6R)-6-[(R)-(−)-2-amino-2-(p-hydroxyphenyl)acetamido]-3,3-dimethyl-7-oxo4-thia-1-azabicyclo [3.2.0] heptane-carboxylic acid. The term includes all pharmaceutically acceptable hydrates (e.g., trihydrate), crystalline forms, and salts thereof. Amoxicillin is shown below:

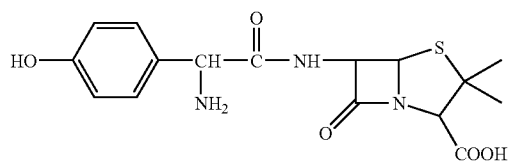

As used herein, a "polymer of a beta-lactam antibiotic" refers to the product formed from the condensation of two or more (e.g., 2, 3, 4, or 5) beta-lactam antibiotic (e.g. amoxicillin) molecules. The condensation can occur with any synthetically feasible reactive group, for instance with the phenol group and the carboxylic acid group of amoxicillin, or with the amino group and the carboxylic acid group of amoxicillin.

As used herein, a "divalent radical of a beta-lactam antibiotic" refers to a beta-lactam antibiotic (as defined herein) having two open valences. These two open valences can be derived from any two of the synthetically suitable functional groups (e.g., phenol group, amino group, carboxylic acid group, hydroxyl group, sulfate group, phosphate group, or mercapto group) present on the beta-lactam antibiotic. For example, the two open valences can be derived from the phenol group and the carboxylic acid group; from the phenol group and the amino group; or from the amino group and the carboxylic acid group of amoxicillin. Specifically, the two open valences can be derived from the phenol group and the carboxylic acid group of amoxicillin, as shown below:

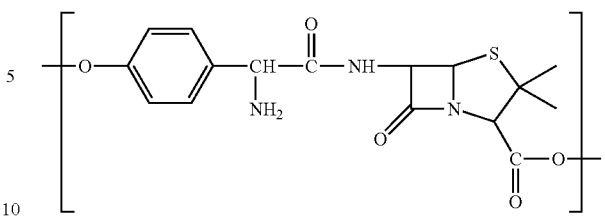

As used herein, a "divalent radical of a polymer of a beta-lactam antibiotic" refers to a polymer of a beta-lactam antibiotic (as defined herein) having two open valences. These two open valences can be derived from any two of the synthetically suitable functional groups (e.g., phenol group, amino group, thiol group, hydroxyl group, and carboxylic acid group) present on the polymer of the antibiotic. For example, the two open valences can be derived from the phenol group and the carboxylic acid group; from the phenol group and the amino group; or from the amino group and the carboxylic acid group of amoxicillin. Specifically, the two open valences can be derived from the phenol group and the carboxylic acid group of amoxicillin.

As used herein, "clavulanic acid" refers to the β lactamase inhibitor chemically designated as (Z)-(2R,5R)-3-(2-hydroxyethylidene)-7-oxo4-oxa-1-azabicyclo[3.2.0]-heptane-2-carboxylic acid. The term includes all pharmaceutically acceptable hydrates, crystalline forms, and salts (e.g., potassium) thereof. Clavulanic acid is shown below:

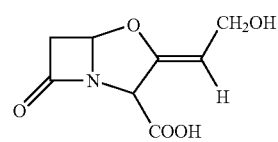

As used herein, a "polymer of a beta-lactamase inhibitor" refers to the product formed from the condensation of two or more (e.g., 2, 3, 4, or 5) beta-lactamase inhibitor (e.g. clavulanic acid) molecules. The condensation can occur with any two synthetically feasible reactive groups of the beta-lactamase inhibitor, e.g., the hydroxyl group and the carboxylic acid group of clavulinic acid.

As used herein, a "divalent radical of a beta-lactamase inhibitor" refers to a beta-lactamase inhibitor (as defined herein) having two open valences. These two open valences can be derived from any two synthetically suitable functional groups present on the beta-lactamase inhibitor (e.g., the hydroxyl group and the carboxylic acid group of clavulanic acid as shown below):

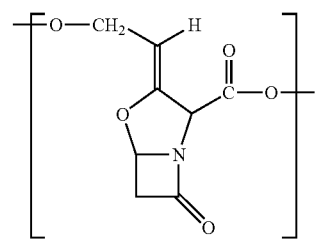

As used herein, a "divalent radical of a polymer of a beta-lactamase inhibitor" refers to a polymer of a beta-lactamase inhibitor (as defined herein) having two open valences. These two open valences can be derived from the two synthetically suitable functional groups (e.g., hydroxyl group and the carboxylic acid group of clavulanic acid) present on the polymer of the beta-lactamase inhibitor.

As used herein, a "copolymer of a beta-lactam antibiotic and a beta-lactamase inhibitor" refers to the product formed from the condensation of one or more (e.g., 1, 2, 3, or 4) beta-lactam antibiotic molecules and one or more (e.g., 1, 2, 3, or 4) beta-lactamase inhibitor molecules. The condensation can occur with synthetically suitable functional groups of the beta-lactam antibiotic (e.g., the phenol group, the amino group and/or the carboxylic acid group of amoxicillin) and synthetically suitable functional groups of the beta-lactamase inhibitor (e.g., the hydroxyl group and/or the carboxylic acid group of clavulanic acid). Specifically, the condensation can occur with: (1) the phenol group of amoxicillin and the carboxylic acid group of clavulanic acid; (2) the amino group of amoxicillin and the carboxylic acid group of clavulanic acid; and/or the carboxylic acid group of amoxicillin and the hydroxyl group of clavulanic acid. Such a copolymer of a beta-lactamase inhibitor and a beta-lactam antibiotic acid can be, for example, a random block copolymer.

As used herein, a "divalent radical of a copolymer of a beta-lactam antibiotic and a beta-lactamase inhibitor" refers to a copolymer of a beta-lactam antibiotic and a beta-lactamase inhibitor (as defined herein) having two open valences. These two open valences can be derived from any two synthetically suitable functional groups present on the copolymer of a beta-lactam antibiotic and a beta-lactamase inhibitor (e.g., hydroxyl group, amino group, phenol group, thiol group, sulfate group, phosphate group, or carboxylic acid group) present on the copolymer of a beta-lactam antibiotic and a beta-lactamase inhibitor.

Each of the beta-lactam antibiotic and the beta-lactamase inhibitor (or a pharmaceutically acceptable salt thereof) can be chemically incorporated into the polymer of the invention if each possesses at least two functional groups that can each be chemically incorporated into a hydrolyzable linkage (e.g., an ester, thioester, anhydride, amide, phosphate ester, or sulfate ester linkage) of the polymer, such that, upon hydrolysis of the polymer, a combination of the beta-lactam antibiotic and the beta-lactamase inhibitor, or a pharmaceutically acceptable salt thereof, is obtained.

Linker "L"

One embodiment of the invention provides a polymer of the invention which is a polymer comprising one or more subunits of formula (I):

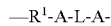
—$R^1$-A-L-A-     (I)

wherein $R^1$ is a divalent radical of a beta-lactam antibiotic, a beta-lactamase inhibitor, a polymer thereof, or a copolymer thereof; each A is independently an ester linkage, a thioester linkage, an amide linkage, an anhydride linkage, a phosphate ester linkage, or a sulfate ester linkage; and L is a linker. In a preferred embodiment, each A is independently an ester linkage, a thioester linkage, an amide linkage, or an anhydride linkage.

The nature of the linker "L" in a polymer of the invention is not critical provided the polymer of the invention possesses acceptable mechanical properties and release kinetics for the selected application. The linker L is typically a divalent organic radical having a molecular weight of from about 25 daltons to about 400 daltons. More preferably, the linker L has a molecular weight of from about 40 daltons to about 200 daltons.

The linker L typically has a length of from about 5 angstroms to about 100 angstroms using standard bond lengths and angles. More preferably, the linker L has a length of from about 10 angstroms to about 50 angstroms.

The linker may be biologically inactive, or may itself possess biological activity. The linker L can also include other functional groups (including hydroxy groups, mercapto groups, amine groups, carboxylic acids, as well as others) that can be used to modify the properties of the polymer. Suitable property modifications of the polymer include, e.g., branching, cross linking, appending other molecules (e.g. another biologically active compound) to the polymer, changing the solubility of the polymer, or effecting the biodistribution of the polymer).

Combination Therapy

The polymers of the invention are useful for administering a combination of a beta-lactam antibiotic and a beta-lactamase inhibitor to a host. Such a combination therapy can be carried out in any one of the following ways:

1) both a beta-lactam antibiotic and a beta-lactamase inhibitor are chemically incorporated into the backbone of the polymer;

2) one of the beta-lactam antibiotic and the beta-lactamase inhibitor is chemically incorporated into the backbone of the polymer, while the other is chemically appended to the polymer of the invention (i.e. not in the backbone of the polymer);

3) one of the beta-lactam antibiotic and the beta-lactamase inhibitor is chemically incorporated into the backbone of the polymer, while the other is physically dispersed within the polymer matrix;

4) both the beta-lactam antibiotic and the beta-lactamase inhibitor are chemically incorporated into the backbone of the polymer, and at least one of a beta-lactam antibiotic and a beta-lactamase inhibitor (which may be the same or different from the beta-lactam antibiotic and beta-lactamase inhibitor that are chemically incorporated into the backbone of the polymer) is chemically appended to the polymer (i.e., not in the backbone of the polymer); or 5) both the beta-lactam antibiotic and the beta-lactamase inhibitor are chemically incorporated into the backbone of the polymer; and at least one of a beta-lactam antibiotic and a beta-lactamase inhibitor (which may be the same or different from the beta-lactam antibiotic and beta-lactamase inhibitor that are chemically incorporated into the backbone of the polymer) is physically dispersed within the polymer matrix.

Specific and Preferred Values

Specific and preferred values listed herein for radicals, substituents, groups, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$ alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

In a specific embodiment of the polymer of the invention, at least one group that will yield the beta-lactam antibiotic and at least one group that will yield the beta-lactamase inhibitor are chemically incorporated into the backbone of the polymer.

In another specific embodiment of the polymer of the invention, at least one group that will yield the beta-lactam antibiotic or at least one group that will yield the beta-lactamase inhibitor is chemically appended to the polymer.

In another specific embodiment of the polymer of the invention, at least one group that will yield the beta-lactam antibiotic or at least one group that will yield the beta-lactamase inhibitor is physically dispersed within the polymer matrix.

Specific beta-lactam antibiotics that can be incorporated into the polymer of the invention include amoxicillin, ampicillin, penicillin, cefadroxil, cephalothin, cephapirin, cephradine, cefamondole, cefixime, cefinetazole, cefonicid, ceforanide, cefotetan, cefoxitin, cefprodoxime, cefprozil, cefuroxime, lorabid, cefdinir, cefixime, cefoperazone, cefotaxime, cefpodoxime, ceftiofur, ceftazadime, ceftibuten, ceftizoxime, mozalactam, cefepime, cefizoxime, ceflacor, cilastatin, imipenem, meropenem, aztreonam, thienamycin, loracarbef, cefotatan, ceftazidime, cephazolin, cephalexin, cephapiria, cefaclor, piperacillin, or a combination thereof.

Specific beta-lactamase inhibitors that can be incorporated into the polymer of the invention include clavulanic acid, sulbactam, or tazobactam. Other known beta-lactamase inhibitors that can be incorporated into the polymer of the invention include derivatives or analogs of clavulanic acid including deoxyclavulanic acid, isoclavulanic acid, 9-deoxyclavulanic acid, 9-amino deoxyclavulanic acid, and other clavulanic acid derivatives such as those wherein the 9-hydroxy group has been chemically modified (e.g., as an acetate, n-methyl carbamate, methyl ether, benzyl ether, or thiomethyl ether). Other beta-lactamase inhibitors that can be used in the polymer of the invention include olivanic acids and thienamycin of the carbapenem family of beta-lactam antibiotics.

A beta-lactamase inhibitor or beta-lactam antibiotic that possesses two reactive functional groups (e.g., an amino group, a hydroxyl group, carboxylic acid group, a thiol group, a —SO$_3$H group, a —PO$_3$H$_2$ group, or a phenol group) can be incorporated into the backbone of the polymer of the invention, can be appended to the polymer of the invention by a hydrolyzable bond, or can be dispersed in the polymer of the invention. A beta-lactamase inhibitor or beta-lactam antibiotic that possesses one reactive functional group can be appended to the polymer of the invention by a hydrolyzable bond, or can be dispersed in the polymer of the invention. A beta-lactames inhibitor or beta-lactam antibiotic that possesses no reactive functional groups can be dispersed in the polymer of the invention. Thus, for instance, among beta-lactam antibiotics, amoxicillin has three reactive groups (a carboxy, an amino, and a phenol) and thus can be incorporated into the backbone of the polymers, appended to the polymers, or dispersed in the polymers. Ampicillin has a carboxy group and an amino group, and thus can be incorporated into the backbone of the polymers, appended to the polymers, or dispersed in the polymers.

Among the beta-lactamase inhibitors, clavulanic acid has two reactive groups (a carboxy group and a hydroxyl) and thus can be incorporated into the backbone of the polymers, appended to the polymers, or dispersed in the polymers. Tazobactam and sulbactam each have only one reactive functional group, a carboxy group, and thus can be appended to the polymers or dispersed in the polymers.

Using this guidance, it is possible to select beta-lactam antibiotics and beta-lactamase inhibitors for use in the polymers of the invention, and select whether they can be chemically incorporated in the backbone of the polymers, appended to the polymers, or dispersed in the polymers.

In a specific embodiment of the polymer of the invention, the beta-lactam antibiotic is amoxicillin and the beta-lactamase inhibitor is clavulanic acid.

In another specific embodiment of the polymer of the invention, the beta-lactam antibiotic is ampicillin and the beta-lactamase inhibitor is sulbactam.

In a specific embodiment of the polymer of the invention, the one or more groups that will each independently yield a beta-lactam antibiotic, a beta-lactamase inhibitor, a pharmaceutically acceptable salt thereof, or a combination thereof upon hydrolysis of the polymer each independently comprise a divalent radical of the beta-lactam antibiotic, a divalent radical of the beta-lactamase inhibitor, a polymer thereof, or a copolymer thereof.

In a specific embodiment of the polymer of the invention, the backbone of the polymer comprises ester linkages, thioester linkages, amide linkages, anhydride linkages, or a combination thereof.

In a specific embodiment of the polymer of the invention, the backbone of the polymer comprises ester linkages, thioester linkages, amide linkages, or a combination thereof.

In a specific embodiment of the polymer of the invention, the backbone of the polymer comprises anhydride linkages.

A specific polymer of the invention comprises one or more subunits of formula (I):

—R$^1$-A-L-A-  (I)

wherein, R$^1$ is a divalent radical of a beta-lactam antibiotic (e.g., amoxicillin), a divalent radical of a beta-lactamase inhibitor (e.g. clavulanic acid), a polymer thereof, or a copolymer thereof; each A is independently an ester linkage, a thioester linkage, an amide linkage, an anhydride linkage, a sulfate ester linkage, or a phosphate ester linkage; and L is a linker. In a preferred embodiment, each A is independently an ester linkage, a thioester linkage, an amide linkage, or an anhydride linkage.

A specific value for L is a divalent, branched or unbranched, saturated or unsaturated, hydrocarbon chain, having from 1 to about 25 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of (C$_1$-C$_6$)alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, azido, cyano, nitro, halo, hydroxy, oxo, carboxy, aryl, aryloxy, heteroaryl, and heteroaryloxy.

Another specific value for L is (C$_1$-C$_6$)alkyl, (C$_2$-C$_6$)alkenyl, (C$_2$-C$_6$)alkynyl, (C$_3$-C8)cycloalkyl, or (C$_6$-C$_{10}$)aryl, optionally substituted on carbon with one or more (e.g. 1, 2, 3, or 4) substituents selected from the group consisting of (C$_1$-C$_6$)alkoxy, (C$_3$-C$_6$)cycloalkyl, (C$_1$-C$_6$)alkanoyl, (C$_1$-C$_6$)alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy.

Another specific value for L is a peptide.

Another specific value for L is an amino acid.

Another specific value for L is a divalent, branched or unbranched, saturated or unsaturated, hydrocarbon chain, having from 3 to 15 carbon atoms.

Another specific value for L is a divalent, branched or unbranched, hydrocarbon chain, having from 3 to 15 carbon atoms.

Another specific value for L is a divalent, branched or unbranched, hydrocarbon chain, having from 6 to 10 carbon atoms.

Another specific value for L is a divalent hydrocarbon chain having 7, 8, or 9 carbon atoms.

Another specific value for L is a divalent hydrocarbon chain having 8 carbon atoms.

A specific value for A is an ester linkage, a thioester linkage, or an amide linkage.

Another specific value for A is an anhydride linkage.

A specific value for $R^1$ is a monomer of the beta-lactam antiobiotic or the beta-lactamase inhibitor.

Another specific value for $R^1$ is a polymer of the beta-lactam antiobiotic or the beta-lactamase inhibitor.

Another specific value for $R^1$ is a copolymer of the beta-lactam antiobiotic or the beta-lactamase inhibitor.

Another specific value for $R^1$ is a copolymer of the beta-lactam antiobiotic and the beta-lactamase inhibitor.

Another specific value for $R^1$ is a copolymer of two or more beta-lactam antiobiotics or a copolymer of two or more the beta-lactamase inhibitors.

In a specific embodiment of the polymers of the invention, the polymer comprises two or more beta-lactam antibiotics, two or more beta-lactamase inhibitors, or two or more beta-lactam antibiotics and two or more beta-lactamase inhibitors.

In a specific embodiment of a pharmaceutical composition comprising a polymer of the invention and a pharmaceutically acceptable carrier, the composition provides sustained release of the beta-lactam antibiotic or the beta-lactamase inhibitor, or both.

In a specific embodiment, the composition, when implanted in a body of a mammal, releases at least 250 mg of the beta-lactam antibiotic after the first 12 hours after implantation, releases at least 125 mg of the beta-lactamase inhibitor after the first 12 hours after implantation, or releases at least 250 mg of the antibiotic and at least 125 mg of the beta-lactamase inhibitor after the first 12 hours after implantation.

In a specific embodiment, the composition, when implanted in a body of a mammal, releases at least 500 mg of the beta-lactam antibiotic after the first 24 hours after implantation, releases at least 250 mg of the beta-lactamase inhibitor after the first 24 hours after implantation, or releases at least 500 mg of the antibiotic and at least 250 mg of the beta-lactamase inhibitor after the first 24 hours after implantation.

In a specific embodiment, the composition of the invention is formulated to releases at least 500 mg of the beta-lactam antibiotic and at least 250 mg of the beta-lactamase inhibitor within 24 hours of administration.

Preparation of Polymer Backbones

Processes for preparing polymer backbones of the invention are provided as further embodiments of the invention and are illustrated by the following procedures in which the meanings of the generic radicals are as given above unless otherwise qualified.

A polymer backbone, or a subunit thereof, can be prepared, for example, as illustrated in Scheme I, from a compound of formula $(X^1-R^1-X^2)$ and a linker precursor of formula $(Z^1-L-Z^2)$, wherein $X^1$, $X^2$, $R^1$, $Z^1$, $Z^2$ and n are selected from the values provided below. Each compound of formula $(X^1-R^1-X^2)$ is independently a beta-lactam antibiotic, a beta-lactamase inhibitor, or a pharmaceutically acceptable salt thereof.

Scheme I $$X^2-R^1-X^1 \; + \; Z^1-L-Z^2 \longrightarrow$$
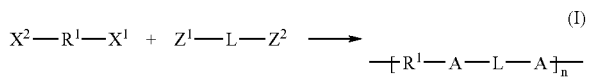

wherein, n is 1 to about 1,000;

$X^2$ is carboxylic acid, hydroxyl, amino, —NHR, phenol, thiol, sulfate group, or phosphate group, or a pharmaceutically acceptable salt thereof;

$X^1$ is carboxylic acid, hydroxyl, amino, —NHR, phenol, thiol, sulfate group, phosphate group or a pharmaceutically acceptable salt thereof;

each $R^1$ is independently a divalent radical of a beta-lactam antibiotic, a divalent radical of a beta-lactamase inhibitor, or a pharmaceutically acceptable salt thereof;

$Z^1$ is carboxylic acid, hydroxyl, amino, —NHR, phenol, thiol, sulfate group, or phosphate group or a pharmaceutically acceptable salt thereof;

$Z^2$ is carboxylic acid, hydroxyl, amino, —NHR, phenol, thiol, sulfate group, or phosphate group or a pharmaceutically acceptable salt thereof;

each L is independently a suitable linker, as defined herein above;

each A is independently an ester linkage, a thioester linkage, an amide linkage, an anhydride linkage, a sulfate ester linkage, or a phosphate ester linkage.

Depending on the desired synthetically suitable functional groups ($X^1$ and $X^2$) of the beta-lactam antibiotic, beta-lactamase inhibitor, or a pharmaceutically acceptable salt thereof, corresponding synthetically suitable functional groups ($Z^1$ and $Z^2$) can be selected from the following table, to provide an ester linkage, thioester linkage, an amide linkage, or an anhydride linkage in the polymer backbone.

| Functional Group on Beta-Lactam Antibiotic or Beta-Lactamase Inhibitor, ($X_1$ or $X_2$) | Functional Group on Linker Precursor ($Z_1$ or $Z_2$) | Resulting Linkage in Polymer or Copolymer Backbone (A) |
| --- | --- | --- |
| —COOH | —OH | Ester |
| —COOH | —NHR | Amide |
| —COOH | —SH | Thioester |
| —COOH | —COOH | Anhydride |
| —COOH | —Ar—OH | Aryl Ester |
| —OH | —COOH | Ester |
| —Ar—OH | —COOH | Aryl Ester |
| —NHR | —COOH | Amide |
| —SH | —COOH | Thioester |
| —SO$_3$H | —OH | Sulfate Ester |
| —PO$_3$H$_2$ | —OH | Phosphate Ester |

A specific suitable class of polymer backbones disclosed in Scheme I include, e.g., copolymers prepared as illustrated in Scheme Ia, from a beta-lactam antibiotic (e.g., amoxicillin) represented by the formula $(X^1-R^1-X^2)$, a beta-lactamase inhibitor (e.g., clavulanic acid) represented by the formula ($X^3$—$R^2$—$X^4$), and a linker precursor of formula ($Z^1$-L-$Z^2$); wherein $X^1$, $X^2$, $X^3$, $X^4$ $R^1$, $R^2$, $Z^1$, $Z^2$ and n are selected from the values provided below.

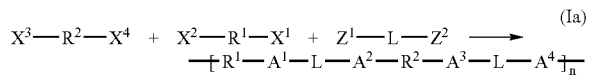

wherein, n is 1 to about 1,000;

$X^2$ is carboxylic acid, hydroxyl, amino, —NHR, phenol, thiol, sulfate group, or phosphate group, or a pharmaceutically acceptable salt thereof;

$X^1$ is carboxylic acid, hydroxyl, amino, —NHR, phenol, thiol, sulfate group, or phosphate group, or a pharmaceutically acceptable salt thereof;

$X^3$ is carboxylic acid, hydroxyl, amino, —NHR, phenol, thiol, sulfate group, or phosphate group, or a pharmaceutically acceptable salt thereof;

$X^4$ is carboxylic acid, hydroxyl, amino, —NHR, phenol, thiol, sulfate group, or phosphate group, or a pharmaceutically acceptable salt thereof;

each $R^1$ is a divalent radical of a beta-lactam antibiotic (e.g., amoxicillin) or a pharmaceutically acceptable salt thereof;

each $R^2$ is a divalent radical of a beta-lactamase inhibitor (e.g., clavulanic acid);

$Z^1$ is carboxylic acid, hydroxyl, amino, —NHR, phenol, thiol, sulfate group, or phosphate group, or a pharmaceutically acceptable salt thereof;

$Z^2$ is carboxylic acid, hydroxyl, amino, —NHR, phenol, thiol, sulfate group, or phosphate group, or a pharmaceutically acceptable salt thereof;

each L is independently a suitable linker, as defined herein above;

each $A^1$ is independently an ester linkage, a thioester linkage, an amide linkage, an anhydride linkage, a sulfate ester linkage, or a phosphate ester linkage; and each $A^2$ is independently an ester linkage, a thioester linkage, an amide linkage, an anhydride linkage, a sulfate ester linkage, or a phosphate ester linkage.

A specific polymer backbone, or a subunit thereof, can be prepared, for example, as illustrated in Scheme II, from amoxicillin represented by the formula ($X^1$—$R^1$—$X^2$) and a linker precursor of formula ($Z^1$-L-$Z^2$), wherein $X^1$, $X^2$, $R^1$, $Z^1$, $Z^2$ and n are selected from the values provided below.

Scheme II

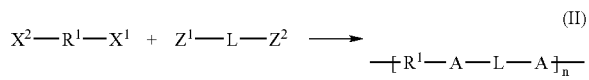

wherein, n is 1 to about 1,000;

$X^2$ is carboxylic acid, amino, phenol, or a pharmaceutically acceptable salt thereof;

$X^1$ is carboxylic acid, amino, phenol, or a pharmaceutically acceptable salt thereof;

each $R^1$ is a divalent radical of amoxicillin, or a pharmaceutically acceptable salt thereof;

$Z^1$ is carboxylic acid, hydroxyl, thiol, amino, phenol, or a pharmaceutically acceptable salt thereof;

$Z^2$ is carboxylic acid, hydroxyl, thiol, amino, phenol, or a pharmaceutically acceptable salt thereof;

each L is independently a suitable linker, as defined herein above;

each A is independently an ester linkage, a thioester linkage, an amide linkage, or an anhydride linkage.

Depending on the desired synthetically suitable functional groups ($X^1$ and $X^2$) of amoxicillin or a pharmaceutically acceptable salt thereof, corresponding synthetically suitable functional groups ($Z^1$ and $Z^2$) can be selected from the following table, to provide an ester linkage, thioester linkage, an amide linkage, or an anhydride linkage in the polymer backbone.

| Functional Group on Amoxicillin ($X_1$ or $X_2$) | Functional Group on Linker Precursor ($Z_1$ or $Z_2$) | Resulting Linkage in Polymer Backbone (A) |
|---|---|---|
| —COOH | —OH | Ester |
| —COOH | —NHR | Amide |
| —COOH | —SH | Thioester |
| —COOH | —COOH | Anhydride |
| —COOH | —Ar—OH | Aryl Ester |
| —Ar—OH | —COOH | Aryl Ester |
| —NHR | —COOH | Amide |

Another specific polymer backbone, or a subunit thereof, can be prepared, for example, as illustrated in Scheme III, from clavulanic acid represented by the formula ($X^1$—$R^1$—$X^2$) and a linker precursor of formula ($Z^1$-L-$Z^2$), wherein $X^1$, $X^2$, $R^1$, $Z^1$, $Z^2$ and n are selected from the values provided below.

Scheme III

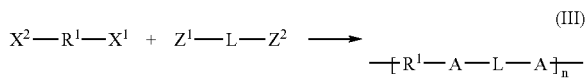

wherein, n is 1 to about 1,000;

$X^2$ is carboxylic acid, hydroxyl, or a pharmaceutically acceptable salt thereof;

$X^1$ is carboxylic acid, hydroxyl, or a pharmaceutically acceptable salt thereof;

each $R^1$ is a divalent radical of clavulanic acid, or a pharmaceutically acceptable salt thereof;

$Z^1$ is carboxylic acid, hydroxyl, thiol, amino, phenol, or a pharmaceutically acceptable salt thereof;

$Z^2$ is carboxylic acid, hydroxyl, thiol, amino, phenol, or a pharmaceutically acceptable salt thereof;

each L is independently a suitable linker, as defined herein above;

each A is independently an ester linkage, a thioester linkage, an amide linkage, or an anhydride linkage.

Depending on the desired synthetically suitable functional groups ($X^1$ and $X^2$) of clavulanic acid or a pharmaceutically acceptable salt thereof, corresponding synthetically suitable functional groups ($Z^1$ and $Z^2$) can be selected from the following table, to provide an ester linkage, thioester linkage, an amide linkage, or an anhydride linkage in the polymer backbone.

| Functional Group on Clavulanic Acid ($X_1$ or $X_2$) | Functional Group on Linker Precursor ($Z_1$ or $Z_2$) | Resulting Linkage in Polymer Backbone (A) |
|---|---|---|
| —COOH | —OH | Ester |
| —COOH | —NHR | Amide |
| —COOH | —SH | Thioester |
| —COOH | —COOH | Anhydride |
| —COOH | —Ar—OH | Aryl Ester |
| —OH | —COOH | Ester |

A polymer backbone which is a polyester, or a polymer backbone comprising a polyester subunit, can be formed from amoxicillin of formula (HO—$R^1$—COOH) and from a linker precursor of formula HO-L-COOH as illustrated in Scheme IV:

Scheme IV

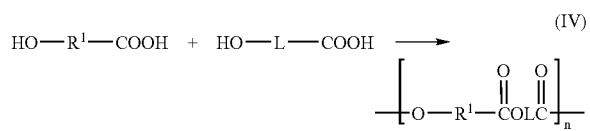

(IV)

wherein, n is 1 to about 1,000;

each $R^1$ is independently a divalent radical of amoxicillin, or a pharmaceutically acceptable salt thereof, such that HO—$R^1$—COOH is amoxicillin, or a pharmaceutically acceptable salt thereof; and each L is independently a suitable linker, as defined herein above.

A polymer backbone which is a polyester, or a polymer backbone comprising a polyester subunit, can be formed from clavulanic acid of formula (HO—$R^1$—COOH) and from a linker precursor of formula HO-L-COOH as illustrated in Scheme V:

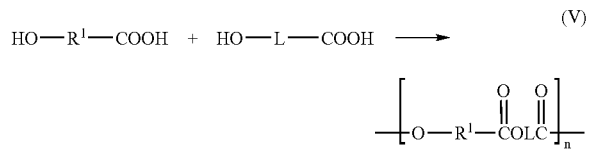

(V)

wherein, n is 1 to about 1,000;

each $R^1$ is independently a divalent radical of clavulanic acid, such that HO—$R^1$—COOH is clavulanic acid; and each L is independently a suitable linker, as defined herein above.

A polymer backbone which is a polyamide, or a polymer backbone comprising a polyamide subunit, can be formed from amoxicillin of formula ($H_2N$—$R^1$—COOH) and from a linker precursor of formula $H_2N$-L-COOH as illustrated in Scheme VI:

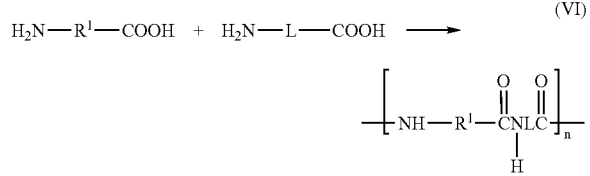

(VI)

wherein, n is 1 to about 1,000;

each $R^1$ is independently a divalent radical of amoxicillin, or a pharmaceutically acceptable salt thereof, such that $H_2N$—$R^1$—COOH is amoxicillin, or a pharmaceutically acceptable salt thereof; and each L is independently a suitable linker, as defined herein above.

The polymer products of schemes I-VI and scheme Ia are polymers of the invention.

It is appreciated that those of skill in the art understand that suitable protecting groups can be used during the reaction illustrated in Schemes I-VI. For example, other functional groups present in the beta-lactam antibiotic, beta-lactamase inhibitor, or a pharmaceutically acceptable salt thereof can be protected during polymerization; and the protecting groups can subsequently be removed to provide the polymer backbone. Suitable protecting groups and methods for their incorporation and removal are well known in the art (see for example Greene, T. W.; Wutz, P. G. M. "Protecting Groups In Organic Synthesis" second edition, 1991, New York, John Wiley & sons, Inc.).

Additionally, when a carboxylic acid is reacted with a hydroxyl group, a mercapto group, an amine group, or another carboxylic acid group to provide an ester linkage, thioester linkage, an amide linkage, or an anhydride linkage, the carboxylic acid can be activated prior to the reaction, for example, by formation of the corresponding acid chloride. Numerous methods for activating carboxylic acids, and for preparing ester linkages, thioester linkages, amide linkages, and anhydride linkages are known in the art (see for example Advanced Organic Chemistry: Reaction Mechanisms and Structure, 4 ed., Jerry March, John Wiley & Sons, pages 419-437 and 1281).

Preparation of Polymers of the Invention

Processes for preparing polymers of the invention are provided as further embodiments of the invention and are illustrated by the following procedures in which the meanings of the generic radicals are as given above unless otherwise qualified.

When the polymer backbone (e.g., the copolymers disclosed in Scheme I) includes both a beta-lactam antibiotic and a beta-lactamase inhibitor (or a pharmaceutically acceptable salt thereof), the polymer backbone can effectively serve as a polymer of the invention. Specifically, in such an embodiment, both the beta-lactam antibiotic and beta-lactamase inhibitor (or a pharmaceutically acceptable salt thereof) are chemically incorporated into the backbone of the polymer (or more accurately referred to as a copolymer), and can be released upon degradation of the polymer, under physiological conditions. This polymer backbone can also be used to prepare additional suitable polymer backbones. For example, a random block copolymer of a beta-lactam antibiotic and a beta-lactamase inhibitor can be prepared as shown in Scheme I. This polymer backbone can be further polymerized with any one or more suitable polymer backbones disclosed in Schemes I-VI. Specifically, the random block copolymer of a beta-lactam antibiotic and a beta-lactamase inhibitor can be further polymerized with the polymer backbone (polyester) formed from a beta-lactamase inhibitor and from a linker precursor of formula HO-L-COOH illustrated in Scheme V. Alternatively, the random block copolymer of amoxicillin and clavulanic acid can be further polymerized with the polymer backbone formed from a beta-lactam antibiotic from a linker precursor of formula $H_2N$-L-COOH illustrated in Scheme VI. Alternatively, the random block copolymer of a beta-lactam antibiotic and a beta-lactamase inhibitor can be further polymerized with the polymer backbone (polyester) formed from a beta-lactam antibiotic (e.g. amoxicillin of formula (HO—R¹—COOH)) and from a linker precursor of formula HO-L-COOH illustrated in Scheme IV.

The beta-lactam antibiotic and/or the beta-lactamase inhibitor (or a pharmaceutically acceptable salt thereof) can be chemically appended to the polymer backbone, thereby providing a polymer of the invention. The chemical appendage of the beta-lactam antibiotic and/or the beta-lactamase inhibitor (or the pharmaceutically acceptable salt thereof) to the polymer backbone can occur via the linker present in the polymer backbone (through a synthetically suitable functional group present therein) or can occur via the existing beta-lactam antibiotic and/or beta-lactamase inhibitor present in the polymer backbone (through a synthetically suitable functional group present therein), provided the resulting bonds formed from the chemical appendage can effectively hydrolyze under physiological conditions to release the beta-lactam antibiotic and/or beta-lactamase inhibitor (or a pharmaceutically acceptable salt thereof) that was chemically appended to the polymer backbone.

The beta-lactam antibiotic and/or the beta-lactamase inhibitor (or a pharmaceutically acceptable salt thereof) can be physically dispersed within the polymer backbone, thereby providing a polymer of the invention. The physical dispersion of the beta-lactam antibiotic and/or the beta-lactamase inhibitor (or the pharmaceutically acceptable salt thereof) within the polymer backbone can be accomplished using any suitable technique known to those of skill in the art, provided the resulting polymer matrix can effectively degrade under physiological conditions to release the beta-lactam antibiotic and/or the beta-lactamase inhibitor (or a pharmaceutically acceptable salt thereof) that was physically dispersed within the polymer backbone.

Any of the chemical reactions disclosed herein (e.g. polymerization reactions, copolymerization reactions, and chemically appending a beta-lactam antibiotic and/or a beta-lactamase inhibitor to the polymer backbone) can be carried out using well known synthetic techniques and conditions to provide a polymer of the invention (I) or a polymer backbone. Suitable techniques, reagents, reaction conditions, etc. are disclosed, e.g., in *Advanced Organic Chemistry*, second edition, Part B: Reactions and Synthesis, Carey and Sunberg, Plenum Press, N.Y. (1983); *Advanced Organic Chemistry*, Reactions, Mechanisms, and Structure, second edition, March, McGraw Hill, N.Y. (1977); and *Comprehensive Organic Transformations*, A Guide to Functional Group Preparations, second edition, Larock, N.Y. (1999); and reference cited therein.

Ratio of Beta-Lactam Antibiotic/Beta-Lactamase Inhibitor

Augmentin® (amoxicillin/clavulanate potassium) is commercially available from Glaxo SmithKline Beecham as a powder for oral suspension, chewable tablets, or tablets. The oral suspensions are typically 5 mL suspensions, wherein 125 mg of amoxicillin and 31.5 mg of clavulanic acid as the potassium salt are present; 200 mg of amoxicillin and 28.5 mg of clavulanic acid as the potassium salt are present; 250 mg of amoxicillin and 62.5 mg of clavulanic acid as the potassium salt are present; or 400 mg of amoxicillin and 57.0 mg of clavulanic acid as the potassium salt are present.

The chewable tablets are typically formulated such that 125 mg of amoxicillin and 31.5 mg of clavulanic acid as the potassium salt are present; 200 mg of amoxicillin and 28.5 mg of clavulanic acid as the potassium salt are present; 250 mg of amoxicillin and 62.5 mg of clavulanic acid as the potassium salt are present; or 400 mg of amoxicillin and 57.0 mg of clavulanic acid as the potassium salt are present.

The tablets are typically formulated such that 250 mg of amoxicillin and 125 mg of clavulanic acid as the potassium salt are present; or 500 mg of amoxicillin and 125 mg of clavulanic acid as the potassium salt are present; or 875 mg of amoxicillin and 125 mg of clavulanic acid as the potassium salt are present.

As such, Augmentin® (amoxicillin/clavulanate potassium) typically includes amoxicillin and clavulanic acid as the potassium salt in a molar ratio of greater than about 1.0 (amoxicillin to clavulanic acid as the potassium salt). Specifically, Augmentin® (amoxicillin/clavulanate potassium) typically includes amoxicillin and clavulanic acid as the potassium salt in a molar ratio of about 1.10 to about 4.0, inclusive (amoxicillin to clavulanic acid as the potassium salt). More specifically, Augmentin® (amoxicillin/clavulanate potassium) typically includes amoxicillin and clavulanic acid as the potassium salt in a molar ratio of about 1.131, about 2.263, about 3.960, or about 3.970 (amoxicillin to clavulanic acid as the potassium salt).

The polymers of the present invention can have any suitable and appropriate ratio of beta-lactam antibiotic (e.g., amoxicillin) to beta-lactamase inhibitor (e.g., clavulanic acid) (or a pharmaceutically acceptable salt thereof). In one embodiment of the invention, a polymer of the present invention can have a molar ratio of amoxicillin to clavulanic acid (or a pharmaceutically acceptable salt thereof) substantially identical (e.g., ±0.01%, ±0.001%, or ±0.0001%) to the molar ratio of amoxicillin to clavulanic acid in any one of the Augmentin® (amoxicillin/clavulanate potassium) formulations. In such an embodiment, the ratio of amoxicillin to clavulanic acid (or pharmaceutically acceptable salt thereof) that is released from the polymer upon degradation will be substantially identical (e.g., ±0.01%, ±0.001%, or ±0.0001%) to the molar ratio of amoxicillin to clavulanic acid in the Augmentin® (amoxicillin/clavulanate potassium) formulation.

Specifically, a polymer of the invention can have a molar ratio of amoxicillin to clavulanic acid, or a pharmaceutically acceptable salt thereof, of greater than about 1.0. A polymer of the invention can have a molar ratio of beta-lactamase inhibitor to beta-lactam antibiotic of, or a pharmaceutically acceptable salt thereof, of greater than about 1.0.

Specifically, a polymer of the invention can have a molar ratio of amoxicillin to clavulanic acid, or a pharmaceutically acceptable salt thereof, of about 1.10 to about 4.0, inclusive.

A polymer of the invention can have a molar ratio of beta-lactamase inhibitor to beta-lactam antibiotic of, or a pharmaceutically acceptable salt thereof, of about 1.1 to about 4.0, or about 1.0 to about 15 inclusive.

Specifically, a polymer of the invention can have a molar ratio of amoxicillin to clavulanic acid, or a pharmaceutically acceptable salt thereof, of about 1.131, about 2.263, about 3.960, or about 3.970.

Specifically, a polymer of the invention can have a molar ratio of amoxicillin to clavulanic acid, or a pharmaceutically acceptable salt thereof, of about 1.131 (±0.010), about 2.263 (±0.010), about 3.960 (±0.010), or about 3.970 (±0.010).

Specifically, a polymer of the invention can have a molar ratio of amoxicillin to clavulanic acid, or a pharmaceutically acceptable salt thereof, of about 1.131 (±0.001), about 2.263 (±0.001), about 3.960 (±0.001), or about 3.970 (±0.001).

The polymers and compositions of the invention can be formulated to release a beta-lactam antibiotic and a beta-lactamase inhibitor in a certain ratio in a body of a mammal. The ratio of release of the beta-lactam antibiotic and the beta-lactamase inhibitor may be different than their ratio in the polymer, if, for instance, one group is appended to the polymer and the other is part of the polymer backbone, or one is part of the polymer backbone and the other is dispersed in the polymer, or if they are held in the polymer by different chemical linkages.

In one embodiment, the composition or polymer is formulated to release the beta-lactam antibiotic and the beta-lactamase inhibitor in a molar ratio of greater than about 1.0. In another embodiment, the compostion or polymer is formulated to release the beta-lactam antibiotic and the beta-lactamase inhibitor in a molar ratio of about 1.10 to about 4.0. In particular embodiments, the beta-lactam antibiotic is amoxicillin and the beta-lactamase inhbitior is clavulanic acid.

Bacteria

The polymers of the present invention are useful in killing or inhibiting bacteria. Such inhibition or killing of the bacteria can be accomplished by contacting the bacteria, in vivo or in vitro with an effective amount of the polymers of the invention. The bacteria can be a gram positive bacteria, a gram negative bacteria, and can be an anaerobic bacteria or an aerobic bacteria.

Suitable gram positive bacteria include, e.g., *Staphylococcus aureus* (β-lactamase or non-β-lactamase producing), *Enterococcus faecalis, Staphylococcus epidermidis* (β-lactamase or non-β-lactamase producing), *Staphylococcus saprophyticus* (β-lactamase or non-β-lactamase producing), *Streptococcus pneumoniae, Streptococcus pyogenes*, and viridans group *Streptococcus*.

Suitable gram negative bacteria include, e.g., *Enterobacter* species, *Escherichia coli* (β-lactamase or non-β-lactamase producing), *Haemophilus influenzae* (β-lactamase or non-β-lactamase producing), *Klebsiella* species, *Moraxella catarrhalis* (β-lactamase or non-β-lactamase producing), *Streptococcus pneumoniae, Neisseria gonorrhoeae, Eikenella corrodens* (β-lactamase or non-β-lactamase producing), *Neisseria gonorrhoeae* (β-lactamase or non-β-lactamase producing), and *Proteus mirabilis* (β-lactamase or non-β-lactamase producing).

Suitable anaerobic bacteria include, e.g., *Bacteroides* species including *Bacteroides fragilis* (β-lactamase or non-β-lactamase producing) and *Fusobacterium* species (β-lactamase or non-β-lactamase producing), and *Peptostreptococcus* species.

Suitable bacteria include *Staphylococcus aureus* (β-lactamase or non-β-lactamase producing), *Enterococcus faecalis, Staphylococcus epidermidis* (β-lactamase or non-β-lactamase producing), *Staphylococcus saprophyticus* (β-lactamase or non-β-lactamase producing), *Streptococcus pneumoniae, Streptococcus pyogenes*, viridans group *Streptococcus, Enterobacter* species, *Escherichia coli* or non-β-lactamase producing), *Haemophilus influenzae* (β-lactamase or non-β-lactamase producing), *Klebsiella* species, *Moraxella catarrhalis* (β-lactamase or non-β-lactamase producing), *Streptococcus pneumoniae, Neisseria gonorrhoeae, Eikenella corrodens* (β-lactamase or non-β-lactamase producing), *Neisseria gonorrhoeae* (β-lactamase or non-β-lactamase producing), *Proteus mirabilis* (β-lactamase or non-β-lactamase producing), *Bacteroides* species including *Bacteroides fragilis* (β-lactamase or non-β-lactamase producing) and *Fusobacterium* species (β-lactamase or non-β-lactamase producing), *Peptostreptococcus* species, or a combination thereof.

The polymers of the invention can be administered to a mammal (e.g., human) to treat a bacterial infection. The polymers can be administered over any suitable and effective period of time (e.g., up to once every 24 hours, up to once every 12 hours, up to once every 8 hours, etc.). The bacterial infection can be caused by gram positive bacteria, gram negative bacteria, aerobic bacteria, anaerobic bacteria, or a combination thereof.

The polymers of the invention can also be administered in sustained release form to eliminate the need for frequent dosing. The polymers of the invention can be administered only once or once or twice to treat a bacterial infection. Alternatively, the polymers of the invention can be administered less frequently than once every 24 hours. For instance, they can be administered about once every 3 days, about once every 5 days, about once per week, about once per two weeks, or about once per month, or less often than once per month.

The bacterial infection can be lower respiratory tract infection (caused by β lactamase producing strains of *Haemophilus influenzae* and/or *Moraxella (Branhamella) catarrhalis*), otitis media (caused by β lactamase producing strains of *Haemophilus influenzae* and/or *Moraxella (Branhamella) catarrhalis*), sinusitis (caused by β lactamase producing strains of *Haemophilus influenzae* and/or *Moraxella (Branhamella) catarrhalis*), a skin or skin structure infection (caused by β lactamase producing strains of *Staphylococcus aureus, Escherichia coli*, and/or *Klebsiella* spp.), or a urinary tract infection (caused by β lactamase producing strains of *Escherichia coli, Klebsiella* spp. and/or *Enterobacter* spp.), or an infection caused by any other bacteria in any other part of the body or in the body.

Formulations

The polymers of the invention can be formulated as pharmaceutical compositions and administered to a mammalian host, such as a human patient in a variety of forms adapted to the chosen route of administration, i.e., orally, rectally, or parenterally, by intravenous, intramuscular, intraperitoneal, intraspinal, intracranial, topical or subcutaneous routes. For some routes of administration, the polymer can conveniently be formulated as micronized particles.

Thus, the polymers of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the polymer of the invention may be combined with one or more excipients and used in the form of ingestible tablets, buccal tablets, troches, capsules, elixirs, suspensions, syrups, wafers, and the like. Such compositions and preparations preferably contain at least 0.1% of the polymer of the invention by weight. The percentage of the compositions and preparations may, of course, be varied and may conveniently be between about 2 to about 95% of the weight of a given unit dosage form. The amount of polymer of the invention in such therapeutically useful compositions is such that an effective dosage level will be obtained.

The tablets, troches, pills, capsules, suppositories, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The polymer of the invention may also be administered intravenously, intraspinally, intracranially, intramuscularly, subcutaneously, intraocularly, or intraperitoneally by infusion or injection. Solutions of the polymer can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The polymer of the invention may also be used as a coating on a medical device, or as a part or all of a medical device implanted or otherwise used in or upon the body.

The pharmaceutical dosage forms suitable for injection or infusion can include sterile aqueous solutions or dispersions or sterile powders comprising the active ingredient (polymers of the invention) which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the polymer of the invention in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient (polymers of the invention) plus any additional desired ingredient present in the previously sterile-filtered solutions.

For topical administration, the polymers of the invention can be applied in pure form. However, it will generally be desirable to administer them as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the polymers of the invention can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the polymers of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Dosages

Useful dosages of the polymers of the invention can be determined by comparing their in vitro activity, and in vivo activity of the polymers of the invention in animal models. Methods for the extrapolation of effective dosages in mice, and other animals, to humans are known to the art; for example, see U.S. Pat. No. 4,938,949. Additionally, useful dosages can be determined by measuring the rate of hydrolysis for a given polymer of the invention under various physiological conditions. The amount of a polymer required for use in treatment will vary not only with the particular polymer selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Activity

The ability of a polymer of the invention to produce a given therapeutic effect can be determined using in vitro and in vivo pharmacological models which are well known to the art.

The invention will now be illustrated by the following non-limiting examples.

EXAMPLE 1

As illustrated below, 6-Aminopenicillanic (1 g, 2 eqv.) was treated with pyridine (25 ml) and sebacoyl chloride (0.5 mL, 1 eqv) and allowed to react for 24 hours to provide the diacid 1 below. Diacid 1 was treated with acetic anhydride at room temperature for one hour to provide the (bis)anhydride 2, which was polymerized under melt conditions at 160 degrees and 2 mm Hg for 4 hours to provide the anhydride polymer 3.

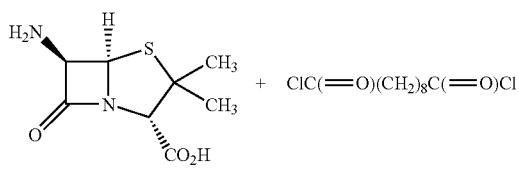

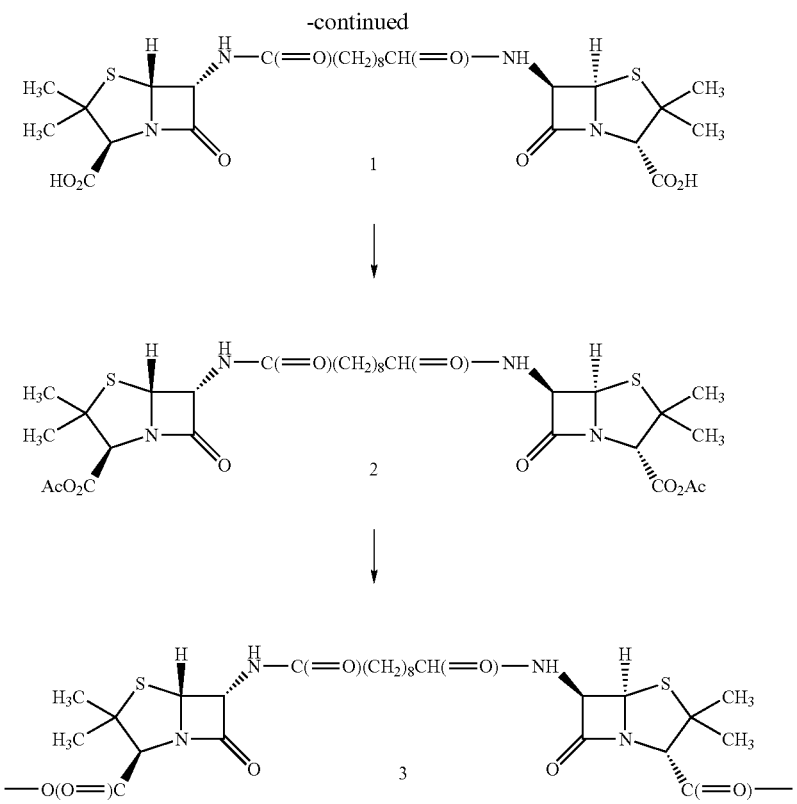

EXAMPLE 2

As illustrated below, clavulinic acid (2 eqv.) can be treated with pyridine (excess) and sebacoyl chloride (1 eqv) to provide the diacid 4 below. Diacid 4 can be treated with acetic anhydride to provide the (bis)anhydride 5, which can be polymerized under melt conditions to provide the anhydride polymer 6.

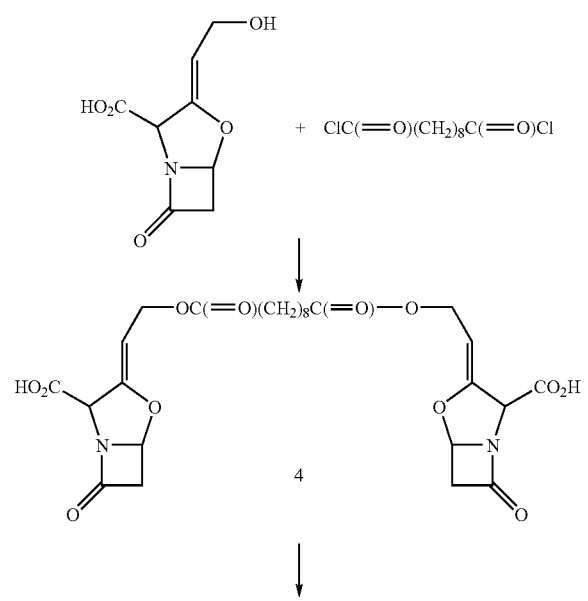

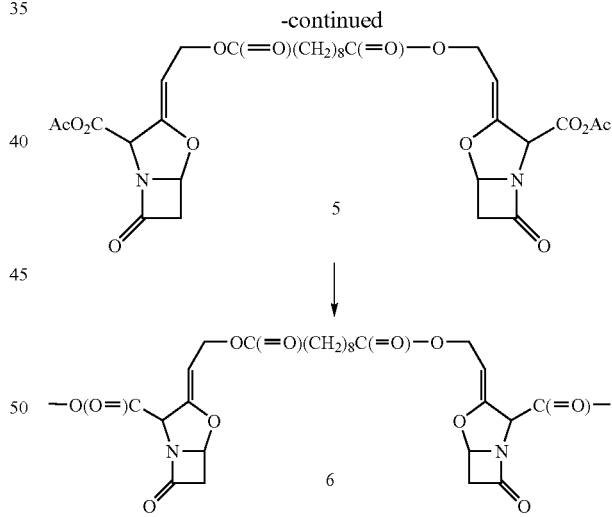

EXAMPLE 3

As illustrated below, the primary amine of amoxicillin (2 eqv.) can be protected (t-Boc) and the resulting material can be treated with pyridine (excess) and sebacoyl chloride (1 eqv) to provide the diacid 7 below. Diacid 7 can be treated with acetic anhydride to provide the (bis)anhydride-8, which can be polymerized under melt conditions and deprotected to provide the anhydride polymer 9

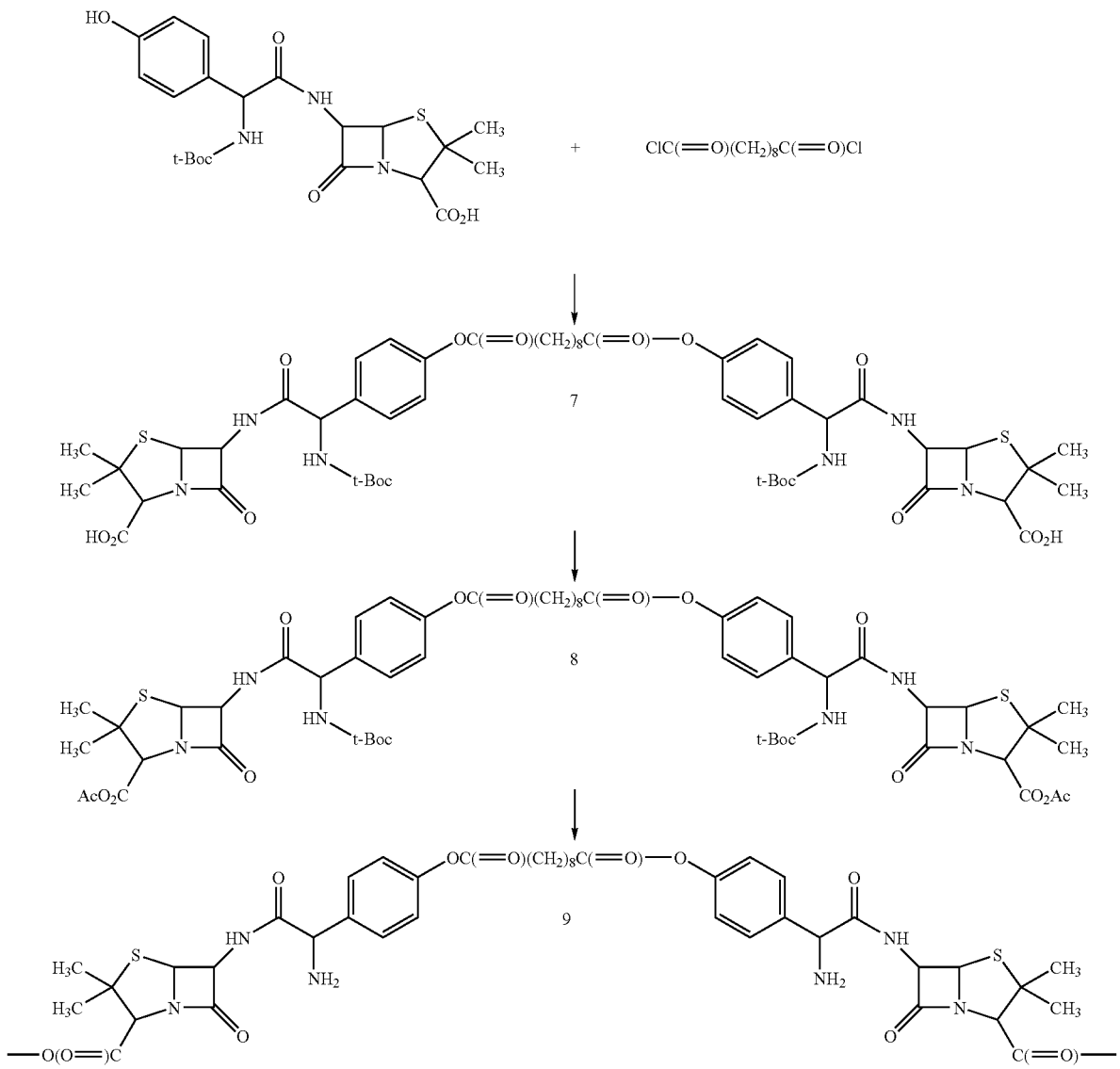

In examples 2 and 3 the sulfur equivalent of sebacoyl chloride can be substituted to provide the corresponding thioester polymers.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A polymer comprising a backbone, wherein the polymer comprises (i) a group that will yield a beta-lactam antibiotic or a pharmaceutically acceptable salt thereof, and (ii) a group that will yield a beta-lactamase inhibitor selected from clavulanic acid, sulbactam, or tazobactamor or a pharmaceutically acceptable salt thereof, upon hydrolysis of the polymer; wherein the group that will yield a beta-lactam antibiotic or a pharmaceutically acceptable salt thereof, or the group that will yield the beta-lactamase inhibitor or a pharmaceutically acceptable salt thereof is chemically incorporated into the backbone of the polymer.

2. The polymer of claim 1 wherein at least one group that will yield the beta-lactam antibiotic and at least one group that will yield the beta-lactamase inhibitor are chemically incorporated into the backbone of the polymer.

3. The polymer of claim 1 wherein at least one group that will yield the beta-lactam antibiotic or at least one group that will yield the beta-lactamase inhibitor is chemically appended to the polymer.

4. The polymer of claim 1 wherein at least one group that will yield a beta-lactam antibiotic is chemically incorporated into the backbone of the polymer.

5. The polymer of claim 1 wherein at least one group that will yield a beta-lactamase inhibitor is chemically incorporated into the backbone of the polymer.

6. The polymer of claim 1 wherein the beta-lactam antibiotic is amoxicillin.

7. The polymer of claim 1 wherein the beta-lactam antibiotic is amoxicillin, ampicillin, penicillin, cefadroxil, cephalothin, cephapirin, cephradine, cefamondole, cefixime, cefmetazole, cefonicid, ceforanide, cefotetan, cefoxitin, cefprodoxime, cefprozil, cefuroxime, lorabid, cefdinir, cefixime, cefoperazone, cefotaxime, cefpodoxime, ceftiofur, ceftazadime, ceftibuten, ceftizoxime, mozalactam, cefepime, cefizoxime, ceflacor, cilastatin, imipenem, meropenem, aztreonam, thienamycin, loracarbef, cefotatan, ceftazidime, cephazolin, cephalexin, cephapiria, cefaclor, piperacillin, or a combination thereof.

8. The polymer of claim 1 wherein the beta-lactam antibiotic is amoxicillin and the beta-lactamase inhibitor is clavulanic acid.

9. The polymer of claim 1 wherein the beta-lactam antibiotic is ampicillin and the beta-lactamase inhibitor is sulbactam.

10. The polymer of claim 1 wherein the polymer comprises one or more subunits of formula (I):

$$-R^1\text{-A-L-A-} \tag{I}$$

wherein
R$^1$ is a divalent radical of the beta-lactam antibiotic, a divalent radical of the beta-lactamase inhibitor, a polymer thereof, or a copolymer thereof;
each A is independently an ester linkage, a thioester linkage, an amide linkage, or an anhydride linkage; and
L is a linker.

11. The polymer of claim 1 wherein the polymer comprises one or more subunits of formula (I):

$$-R^1\text{-A-L-A-}-R^1\text{-A-} \tag{I}$$

wherein,
R$^1$ is independently a divalent radical of the beta-lactam antibiotic, a divalent radical of the beta-lactamase inhibitor, a polymer thereof, or a copolymer thereof;
each A is independently an ester linkage, a thioester linkage, an amide linkage, or an anhydride linkage; and
L is a linker.

12. The polymer of claim 10 or 11 wherein the linker is a divalent, branched or unbranched, saturated or unsaturated, hydrocarbon chain, having from 1 to about 25 carbon atoms, wherein one or more of the carbon atoms is optionally replaced by (—O—) or (—NR—), and wherein the chain is optionally substituted on carbon with one or more substituents selected from the group consisting of (C$_1$-C$_6$)alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, azido, cyano, nitro, halo, hydroxy, oxo, carboxy, aryl, aryloxy, heteroaryl, and heteroaryloxy.

13. The polymer of claim 10 or 11 wherein the linker is a divalent, branched or unbranched, saturated or unsaturated, hydrocarbon chain, having from 3 to 15 carbon atoms.

14. The polymer of claim 10 or 11 wherein each A is independently an ester linkage, a thioester linkage, or an amide linkage.

15. The polymer of claim 10 or 11 wherein each A is independently an anhydride linkage.

16. The polymer of claim 10 or 11 wherein the divalent radical is a monomer of the beta-lactam antibiotic or the beta-lactamase inhibitor.

17. The polymer of claim 10 or 11 wherein the divalent radical is a polymer of the beta-lactam antibiotic or the beta-lactamase inhibitor.

18. The polymer of claim 10 or 11 wherein the divalent radical is a copolymer of the beta-lactam antibiotic or the beta-lactamase inhibitor.

19. A pharmaceutical composition comprising a polymer of claim 1 and a pharmaceutically acceptable carrier.

20. The composition of claim 19, wherein the beta-lactam antibiotic is amoxicillin and the beta-lactamase inhibitor is clavulanic acid.

21. The composition of claim 20 which is formulated to release amoxicillin and clavulanic acid in a molar ratio of greater than about 1.0.

22. The composition of claim 21 which is formulated to release amoxicillin and clavulanic acid in a molar ratio of from about 1.0 to about 4.0.

* * * * *